United States Patent
Kikuchi et al.

[19]

[11] Patent Number: 6,072,854
[45] Date of Patent: Jun. 6, 2000

[54] METHOD AND APPARATUS FOR X-RAY TOPOGRAPHY OF SINGLE CRYSTAL INGOT

[75] Inventors: Tetsuo Kikuchi, Tachikawa; Yoshio Machitani, Tokyo, both of Japan

[73] Assignee: Rigaku Corporation, Tokyo, Japan

[21] Appl. No.: 09/117,498

[22] PCT Filed: Dec. 3, 1997

[86] PCT No.: PCT/JP97/04414

§ 371 Date: Jul. 28, 1998

§ 102(e) Date: Jul. 28, 1998

[30] Foreign Application Priority Data

Dec. 4, 1996 [JP] Japan .................................. 8-337658

[51] Int. Cl.[7] .......................... G01N 23/207; C30B 29/06
[52] U.S. Cl. ................... 378/73; 378/71; 378/86; 378/79
[58] Field of Search ................. 378/73, 74, 71, 378/82, 83, 49, 86, 72, 79

[56] References Cited

U.S. PATENT DOCUMENTS

| | | | |
|---|---|---|---|
| 4,710,259 | 12/1987 | Howe et al. | 370/73 |
| 4,788,702 | 11/1988 | Howe et al. | 378/73 |
| 5,187,729 | 2/1993 | Ibe et al. | 378/73 |
| 5,588,034 | 12/1996 | Bowen et al. | 378/73 |
| 5,720,271 | 2/1998 | Hauser | 378/73 |

FOREIGN PATENT DOCUMENTS

| | | |
|---|---|---|
| 61-45178 | 10/1986 | Japan . |
| 62-116243 | 5/1987 | Japan . |
| 62-242845 | 10/1987 | Japan . |
| 3-255948 | 11/1991 | Japan . |
| 3-255951 | 11/1991 | Japan . |
| 5-203592 | 8/1993 | Japan . |
| 85/01349 WO A1 | 3/1985 | WIPO . |

OTHER PUBLICATIONS

The Rigaku Journal, vol. 8, No. 2, 1991, pp. 25–28, Rigaku Corp., Tokyo, Japan.

Applied Physics Letters, vol. 47, No. 12, 1985, M. P. Scott, S. S. Laderman and A. G. Elliott, "Microscopic identification of defects propagating through the center of silicon and indium–doped liquid encapsulated Czochralski grown GaAs using X–ray topography", pp. 1280–1282.

*Primary Examiner*—David P. Porta
*Assistant Examiner*—Drew A. Dunn
*Attorney, Agent, or Firm*—Frishauf, Holtz, Goodman, Langer & Chick, P.C

[57] ABSTRACT

There is disclosed a method for X-ray topography wherein an X-ray topographic image is obtained for an unprocessed single crystal ingot as it is after being produced by Czochralski method to observe crystal dislocations, thereby finding a boundary between a dislocation-appearing area and a dislocation-disappearing area. A scanning stage (34) travels along a direction X to position the observation area of the silicon ingot (22) at the X-ray irradiation site. The silicon ingot (22) is φ-rotated on its axis so that the predetermined crystal lattice plane erects vertically. A traveling table (46) travels along a direction Y to align the rotation center (49) of an ω-rotation table (48) with the peripheral surface of the ingot (22). The ω-rotation and φ-rotation are precisely adjusted while observing diffracted X-rays with an X-ray television camera (26). Then, an X-ray recording medium (66) is mounted on the scanning stage (34). X-rays from an X-ray source (24) are incident on the peripheral surface of the ingot (22) and the scanning stage (34) is scanned by a given scanning width while recording diffraction images on the X-ray recording medium (66), thereby obtaining an X-ray topographic image and finding a boundary between a dislocation-appearing area and a dislocation-disappearing area.

7 Claims, 10 Drawing Sheets

METHOD AND APPARATUS FOR X-RAY TOPOGRAPHY OF SINGLE CRYSTAL INGOT

TECHNICAL FIELD

The present invention relates to a method and apparatus for X-ray topography for observing dislocations in a single crystal ingot, typically a silicon ingot.

BACKGROUND ART

Figure 7:
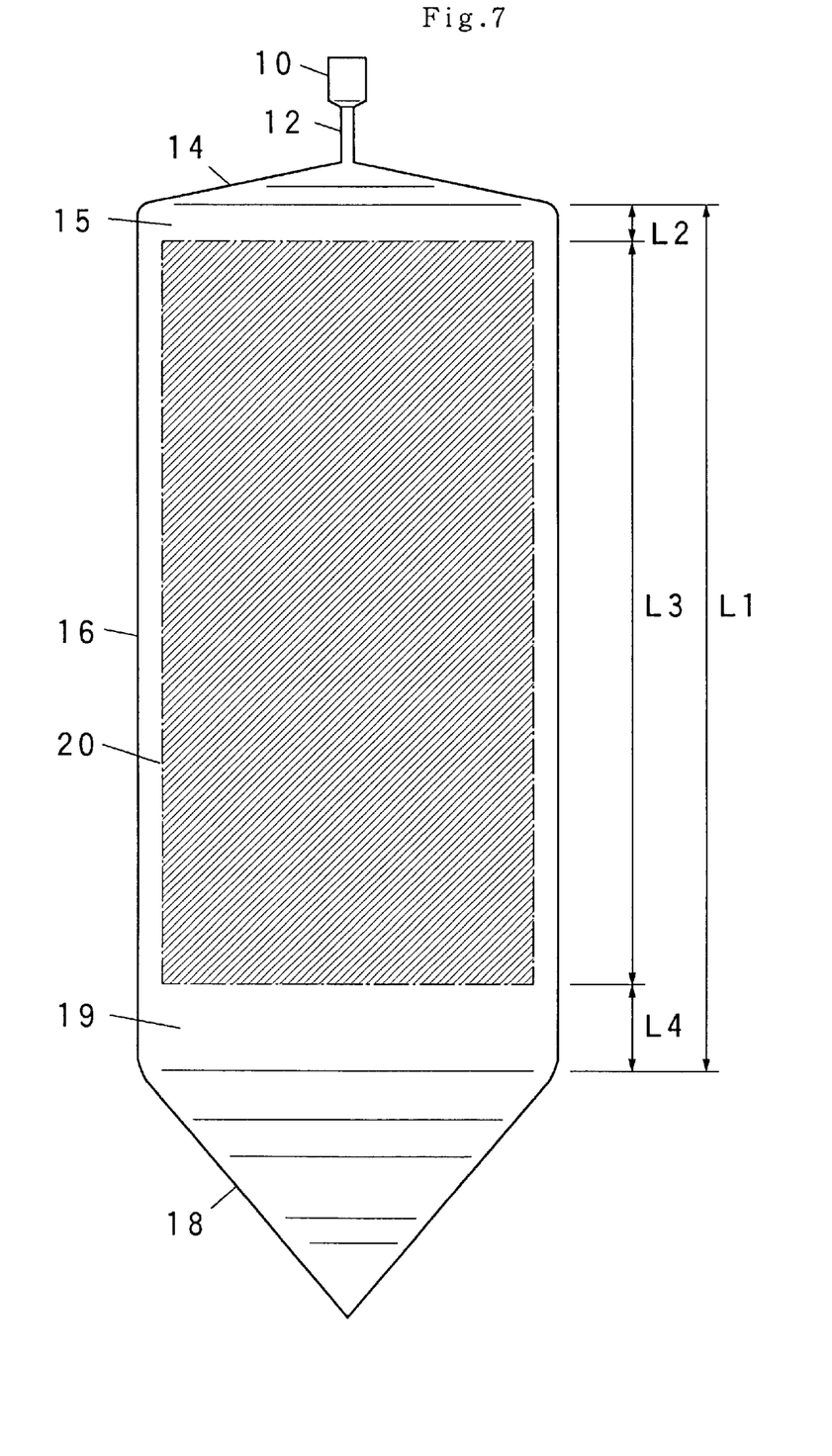
FIG. 7 is a front view of an unprocessed silicon ingot.

Silicon wafers are cut off from silicon single crystal ingots. It has been a recent trend to produce the silicon single crystal ingots by Czochralski method. FIG. 7 shows a front view of an unprocessed silicon ingot as it is after being produced by Czochralski method. The ingot is produced by the steps comprising: (1) dipping a seed crystal 10 (6 to 12 mm in diameter) in silicon melt; (2) pulling up the seed crystal to form a necking 12 (about 2 to 4 mm in diameter and about 50 to 100 mm in length) to eliminate lattice defects such as dislocations and processing defects; (3) forming a shoulder 14 to thicken the crystal to a diameter by about 1% larger than the desired diameter; (4) growing a straight cylindrical body 16 to a desired length; and (5) forming a conical tail 18.

The conical tail 18 is formed so that no dislocations due to thermal distortion are generated in the straight cylindrical body 16. In forming this conical tail 18, the temperature of the melt is raised a little and the pull-up speed is raised. Many dislocations appear in this conical tail 18 due to thermal distortion, often reaching to the straight cylindrical body 16.

A cylindrical useful crystal 20 is cut off from the ingot mentioned above and silicon wafers are produced by slicing this useful crystal 20. The cut-off step is that the shoulder 14 and the conical tail 18 are removed from the silicon ingot, followed by processing the periphery of the straight cylindrical body 16 to adjust its diameter to a desired value. Of the straight cylindrical body 16 (with a length of L1), the region 15 (with a length of L2) close to the shoulder 14 and the region 19 (with a length L4) close to the conical tail 18 are removed since dislocations may appear in these regions due to thermal distortion. Accordingly, the length L3 of the useful crystal 20 becomes shorter than the length L1 of the straight cylindrical body 16. While it is desirable to make the length L3 of the useful crystal 20 as long as possible for the purpose of effectively utilizing the expensive silicon ingot, the risk to incorporate the dislocation-appearing area into the useful crystal 20 is also enhanced when the removed regions 15 and 19 are diminished. Dislocations are liable to appear especially in the region 19 close to the conical tail 18. The regions 15 and 19 to be removed have been rather widely selected larger than the estimated dislocation areas which are based on the empirical estimation. This selection means that a significant amount of the good quality area including no dislocations had been discarded.

It would be possible to take out the maximum useful crystal containing no dislocations provided that the boundary between a dislocation-appearing area and a dislocation-disappearing area could be precisely found. Therefore, it is desired to provide a detection technique that can find the boundary.

There have been known in the art several methods for observing dislocations in a silicon single crystal: for example, (1) a wet-etching method applied to disc-shaped test pieces cut-off from the silicon ingot; and (2) an X-ray topography method applied to thin plates cut-off from the ingot, using forward-reflection X-ray topography (with a Lang camera). These methods, however, require the cut-off test pieces, so that dislocations could not be observed in the unprocessed silicon ingot as it is.

Dislocations could be observed without cutting off the silicon ingot by using, in principle, back-reflection X-ray topography. However, detection of dislocations by the back-reflection X-ray topography have been applied only for the disk-shaped test pieces cut-off from the silicon ingot and no X-ray topographic apparatus are known that can find the boundary between a dislocation-appearing area and a dislocation-disappearing area in the unprocessed silicon ingot which is used as a test sample as it is.

An object of the present invention is to provide a method and apparatus for X-ray topography that can observe dislocations and find the boundary between a dislocation-appearing area and a dislocation-disappearing area in the unprocessed single crystal ingot, typically silicon ingot, by using the ingot as it is as a test sample after being produced by Czochralski method.

DISCLOSURE OF INVENTION

The present invention provides an X-ray topographic method for finding a boundary between a dislocation-appearing area and a dislocation-disappearing area in an unprocessed single crystal ingot as it is after being produced by Czochralski method, comprising the steps of: (a) supporting the unprocessed single crystal ingot rotatably on its axis and movably along its axis; (b) irradiating X-rays to a peripheral surface of the ingot through an incident slit having a long and narrow opening, and obtaining an image of diffracted X-rays from the ingot with an X-ray television camera, followed by setting positional relationship between the ingot and an X-ray optical system so that an optimum image could be obtained; (c) disposing a two-dimensional X-ray recording medium at a position where the diffracted X-rays can be detected; (d) irradiating X-rays to the peripheral surface of the ingot through the incident slit, and scanning the ingot synchronously with the X-ray recording medium in an axial direction of the ingot while recording diffracted X-rays from the ingot; and (e) finding a boundary between a dislocation-appearing area and a dislocation-disappearing area by observing a topographic image recorded on the X-ray recording medium.

The two-dimensional X-ray recording medium may be an X-ray film or an imaging plate.

The X-ray detecting device may have various modifications. The X-ray television camera mentioned above may be substituted by any two-dimensional X-ray imaging device. In this case, a two-dimensional detecting surface such as the X-ray television camera is not always necessary. For example, the detecting device may be a scintillation detector which is moved up and down and right to left. The X-ray recording medium mentioned above may be substituted by any two-dimensional X-ray imaging device for observing an X-ray topographic image: a camera-type X-ray imaging device can be used for example. Furthermore, the two-dimensional X-ray imaging device used for setting may be also used for observing X-ray topographic images.

The two-dimensional X-ray imaging device for X-ray topographic observation may be a camera device capable of obtaining X-ray images as electronic signals. In this case, the X-ray topographic image can be obtained by storing the output signals of the camera device into different memory areas in every given sampling time during scanning the ingot, instead of scanning the X-ray recording medium synchronouly with the ingot. An outline of this electronic method will be described below. A distance (scanning unit-width) where the ingot travels along its axis during a given sampling time is previously determined to allot a different memory area to each scanning unit-width. Then, diffraction images are recorded in each different memory for each given sampling time. After completion of the scanning over a desired scanning area, the signals recorded in the memory areas are joined together to form a single image, thereby obtaining an X-ray topographic image. Thus, the stationary X-ray imaging device can have the same function as scanning of the two-dimensional X-ray recording medium.

The present invention also provides X-ray topographic apparatus for finding a boundary between a dislocation-appearing area and a dislocation-disappearing area in an unprocessed single crystal ingot as it is after being produced by Czochralski method, comprising: (a) two parallel rollers for supporting thereon the unprocessed single crystal ingot rotatably around an axis of the ingot; (b) a scanning stage having the rollers; (c) a scanning mechanism for traveling the scanning stage in an axial direction of the ingot; (d) an incident X-ray optical system including an X-ray source, a collimator connected to the X-ray source, and an incident slit fixed to a tip of the collimator, wherein the incident slit has a long and narrow opening perpendicular to a traveling direction of the scanning stage; (e) an X-ray television camera for obtaining an image of diffracted X-rays from the ingot for the use of setting of an X-ray optical system; (f) a two-dimensional X-ray recording medium for recording the diffracted X-rays from the ingot for the use of recording of an X-ray topographic image; (g) a medium cassette which can support the X-ray recording medium, wherein the X-ray recording medium is positioned selectively in a position on a light path of diffracted X-rays and in a position out of the light path of the diffracted X-rays; (h) a rotary table on which the incident X-ray optical system and the X-ray television camera are mounted, the rotary table being rotatable around a rotation center; (i) an angle-adjustment device allowing the X-ray television camera to rotate on the rotary table around the rotation center so as to adjust an rotary angle; and (j) a traveling table on which the rotary table is mounted, the traveling table being movable in a direction perpendicular to the traveling direction of the scanning stage.

The single crystal ingot produced by Czochralski method may be typically a silicon ingot, but the present invention may be applied for single crystal ingots of other materials.

According to the present invention, crystal dislocations can be observed by obtaining an X-ray topographic image of an unprocessed single crystal ingot as it is after being produced by Czochralski method, so that the boundary between a dislocation-appearing area and a dislocation-disappearing area is found. It was therefore made possible to cut off the single crystal ingot at the boundary, making it possible to cut off the maximum proportion of the good quality crystal area where no dislocations appear.

BRIEF DESCRIPTION OF DRAWINGS

FIGS. 6(A) and (B) show an X-ray topographic image of the silicon ingot.

BEST MODE FOR CARRYING OUT THE INVENTION

Figure 1:
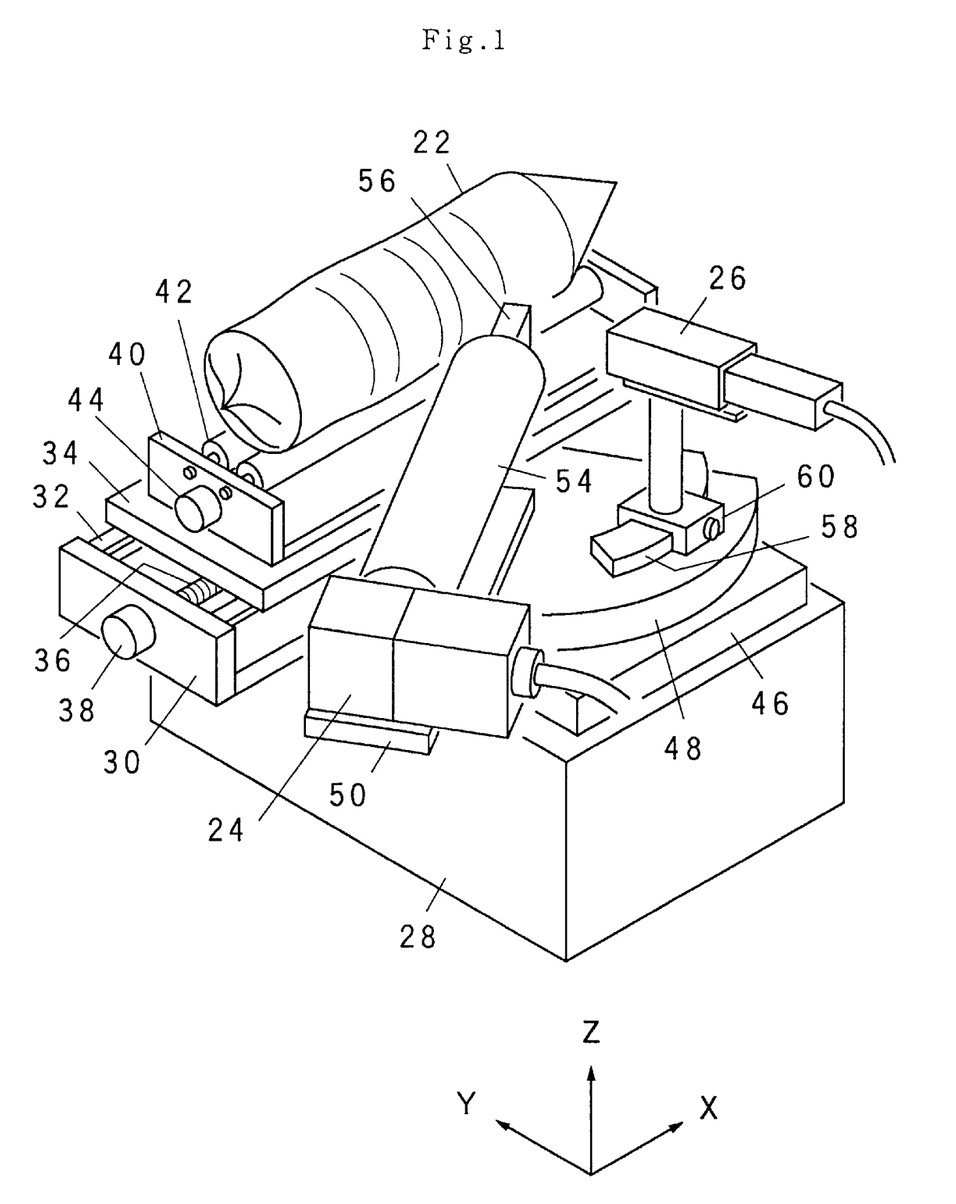
FIG. 1 is a perspective view showing one embodiment of the X-ray topographic apparatus according to the present invention.
Figure 2:
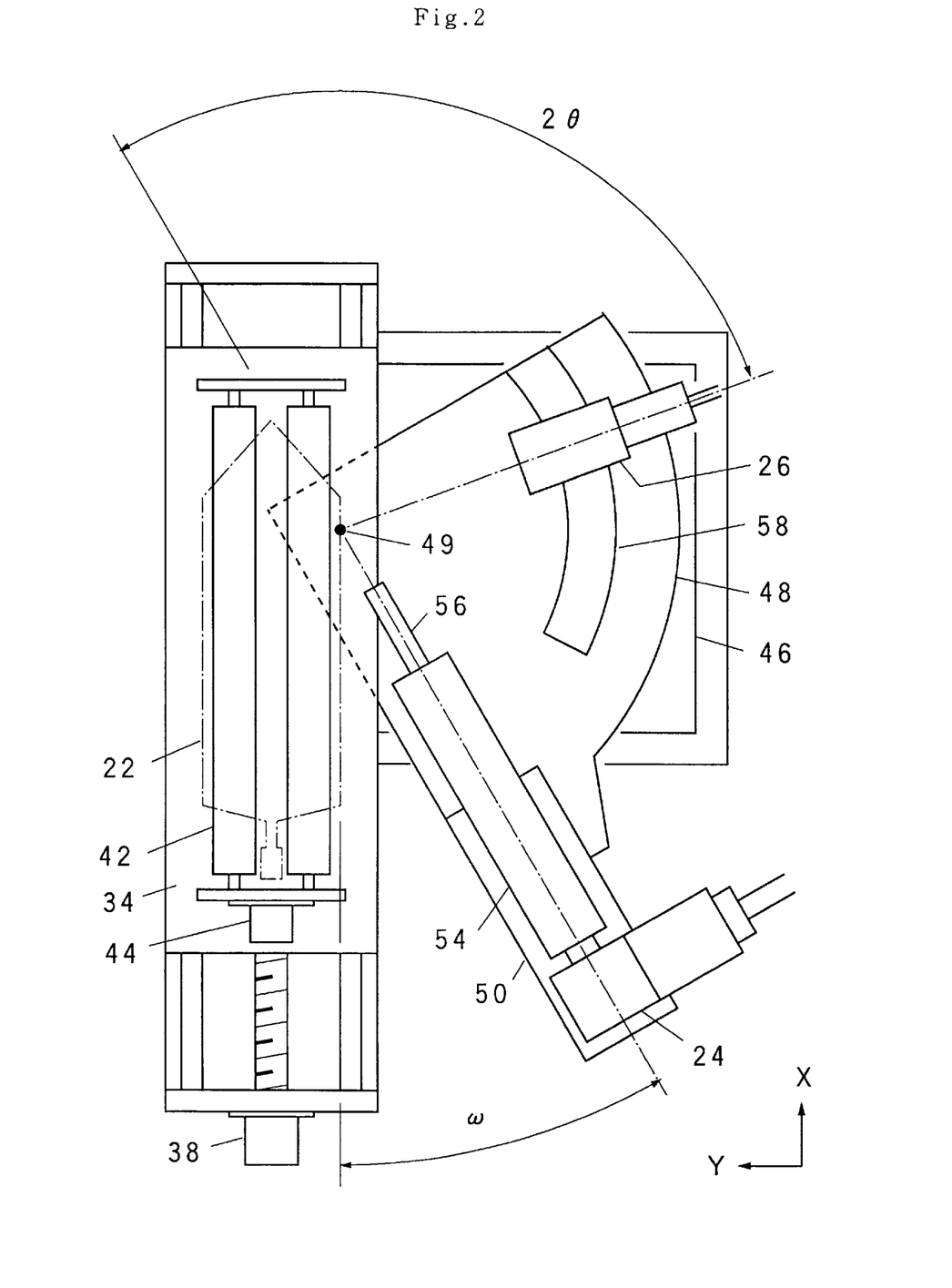
FIG. 2 is a plan view of the apparatus shown in FIG. 1.
Figure 3:
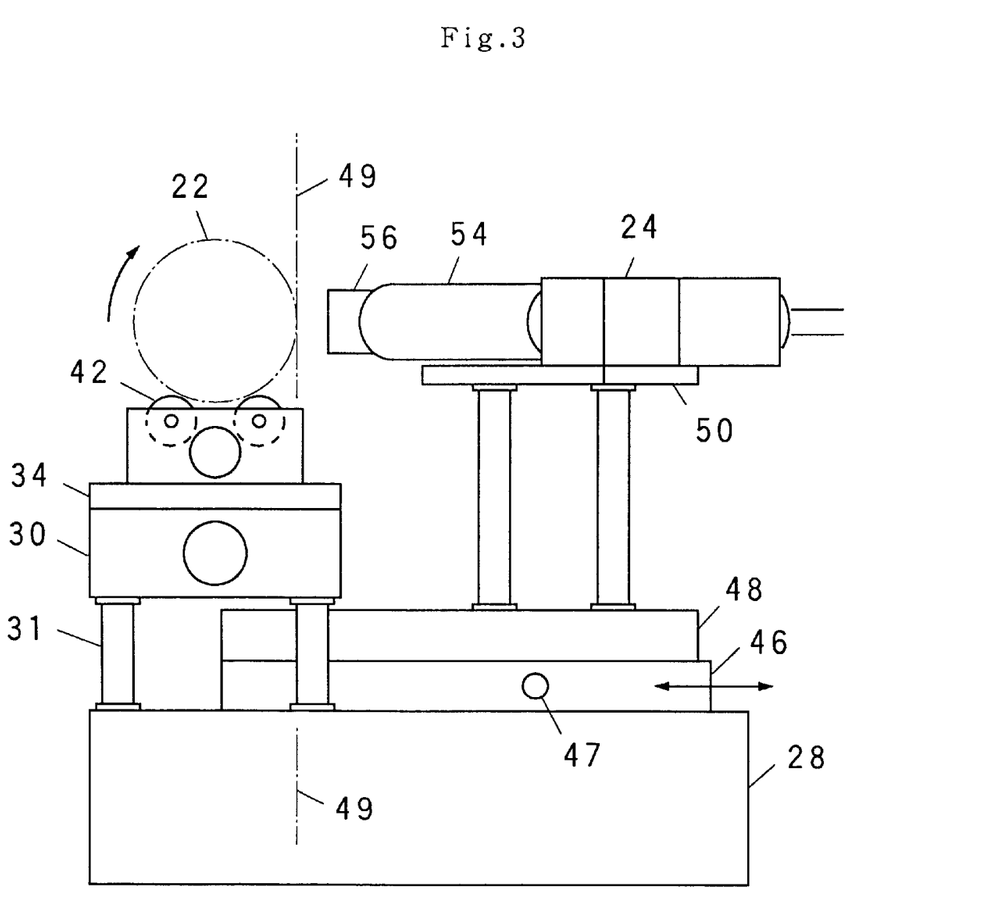
FIG. 3 is a front view of the apparatus shown in FIG. 1.

FIG. 1 is a perspective view of one embodiment of the X-ray topographic apparatus according to the present invention while FIG. 2 and FIG. 3 are its plan view and front view. This X-ray topographic apparatus makes it possible to handle a silicon ingot as a sample as it is after being produced by Czochralski method (that is, the ingot is not processed at all). In the basic function of this apparatus, the silicon ingot 22 can travel along its axis (direction X) and can rotate around its axis. X-rays from an X-ray source are incident on the peripheral surface of the ingot 22. Diffracted X-rays reflected from the ingot are recorded on an X-ray recording medium 66 (an X-ray film or an imaging plate) accommodated in a medium cassette 64 (see FIG. 4). The silicon ingot 22 is scanned synchronouly with the medium cassette 64 in the direction X. An image of the diffracted X-rays is recorded on the X-ray recording medium in the cassette during the scanning, so that an X-ray topographic image is obtained. Since the X-ray diffraction intensity from the dislocation site in the ingot becomes larger than the X-ray diffraction intensity from the area of no dislocations, the dislocation images appear as high-intensity lines on the topographic image. The X-ray television camera 26 is used for setting of the X-ray optical system.

This apparatus can measure X-ray topographic images under such an angular condition that incident X-rays are diffracted at any one of crystal lattice planes of (331), (224), (440) and (135), irrespective of the pull-up orientation of the crystal axis of the silicon ingot. When the pull-up crystal axis is <100>, a measurement for the crystal lattice plane (115) is possible in addition to the measurements for the four crystal lattice planes described above, while a measurement for the crystal lattice plane (333) is possible when the pull-up crystal axis is <111>.

The construction of this apparatus will be described in more detail hereinafter. As shown in FIG. 1, a scanning stage support table 30 is fixed on the top face of a frame 28 by means of four supports 31 (see FIG. 3). Two parallel rails 32 are fixed on a scanning stage support table 30. A scanning stage 34 can travel on the rails 32 in the direction X. The traveling movement of this scanning stage can be used for positioning the observed area of the ingot to the X-ray irradiation site and for scanning the ingot for obtaining a topographic image. A screw shaft 36 is rotatably supported by the scanning stage support table 30. A nut is fixed at the bottom face of this scanning stage 34. The nut engages with the screw shaft 36. The drive shaft of a scanning motor 38 is connected to the screw shaft 36. The scanning motor 38 turns to rotate the screw shaft 36, allowing the scanning stage 34 to travel in the direction X via the nut mentioned above. A crystal support table 40 is fixed on the top face of the scanning stage 34. Two rollers (rubber rollers) 42 are rotatably supported in parallel by the crystal support table 40. The drive shaft of a φ-rotation motor 44 engages with the two rollers 42 via a gear mechanism. The φ-rotation motor 44 turns to rotate the two rollers 42 synchronously with each other in the same direction, allowing the silicon ingot 22 mounted thereon to rotate on its axis. This φ-rotation is used for azimuth adjustment.

On the top face of the frame 28 is mounted a traveling table 46 which can move in the direction Y. On the traveling table 46 is mounted an ω-rotation table 48 which can rotate around its rotation center 49 (see FIG. 3) extending vertically. On the ω-rotation table 48 is fixed an arm 50 on which an X-ray source 24 and a collimator 54 are fixed. The X-ray source 24 is a 2 kW sealed-off X-ray tube with a Cu target, with a normal focus size, and with the point focus in X-ray take-off direction. The collimator 54 is about 1 meter long with the inside evacuated to vacuum. The collimator 54 has an inlet window (X-ray source side) made of beryllium and an outlet window (incident slit side) made of Kepton foil. An incident slit 56 is fixed at the tip of the collimator 54. The opening of the incident slit 56 is long and narrow and extends vertically (direction Z), i.e. the opening is perpendicular to the traveling direction of the scanning stage 34 (direction X). The opening is 100 mm in height along the direction Z and 1 mm in width. The opening of the incident slit 56 is slightly curved as known in the art of X-ray topography (e.g. see Japanese Examined Patent Publication No. 61-45178). Plural kinds of the incident slits are prepared depending on the kind of the crystal lattice planes for which diffracted X-rays will be observed. Five kinds of the slits are prepared for this embodiment: four slits for four crystal lattice planes (331), (224), (440) and (135), and one common slit for crystal lattice planes (333) and (115).

A camera guide 58 is fixed on the ω-rotation table 48. The camera guide is a circular arc in shape with the center coinciding with the rotation center 49 (see FIG. 3). A camera stage 60 engages with the camera guide 58 so as to turn around the rotation center 49 along the camera guide 58. The X-ray television camera 26 is fixed on the camera stage 60. The X-ray television camera 26 converts X-ray images into visible lights via a fluorescent plate, and intensifies optically the visible lights with an image intensifier which is in intimate contact with the fluorescent plate, and observes the visible lights with a lens-coupling CCD camera. The imaging area of the X-ray television camera 26 is a circle with a diameter of about 20 mm. The X-ray television camera 26 in this embodiment is used for setting only of the X-ray optical system, i.e. the camera 26 is used not for obtaining topographic images. The topographic images are recorded on an X-ray recording medium accommodated in a medium cassette mentioned below.

Figure 4:
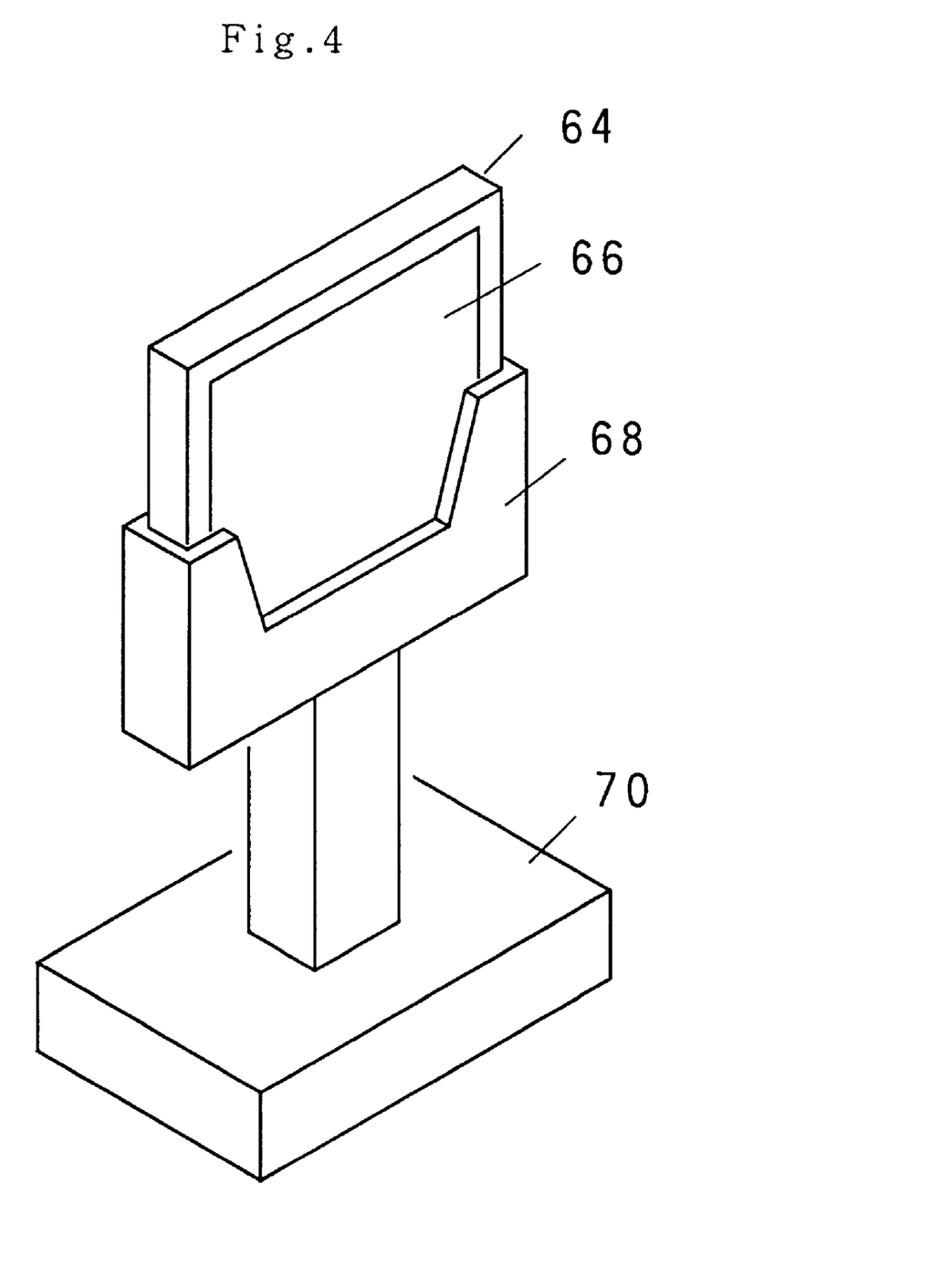
FIG. 4 is a perspective view of the supporting device for the X-ray recording medium.

FIG. 4 is a perspective view of the supporting device for the X-ray recording medium. The five-inch square flat (or two-dimensional) X-ray recording medium 66 is accommodated in a recording medium cassette 64, which can be mounted on a bracket 68. A chuck pedestal 70 is fixed to the bottom end of the bracket 68. A permanent magnet is buried in the bottom face of the chuck pedestal 70 to lock it on the top face of the scanning stage 34 (see FIG. 1). The X-ray recording medium 66 may be an X-ray film or an imaging plate (also referred to as a storage phosphor or a photo-stimulated phosphor).

There will be described hereinafter how to use the X-ray topographic apparatus. Referring to FIG. 2, the X-ray optical system is angularly adjusted first to satisfy the desired diffraction condition. In the case where the pull-up axis of the silicon ingot extends along, for example, a direction <100> of the crystal, the X-ray optical system is angularly adjusted so that X-rays can be diffracted at the crystal plane (115) on the periphery of the silicon ingot. That is, the camera stage 60 (see FIG. 1) first turns along the camera guide 58 so that the X-ray television camera 26 is adjusted at the predetermined diffraction angle 2 θ from the incident X-rays. Then, the ω-rotation table 48 turns so that an X-ray incident angle ω is adjusted at a desired angle from the silicon ingot. The X-ray incident angle ω is adjustable in a range of 20 to 50 degrees in this embodiment.

After completion of the angle adjustment, an unprocessed silicon ingot 22 produced by Czochralski method is mounted on the two rollers 42. In the case where the level of the silicon ingot axis (depending on the diameter of the ingot) is not same as the height of the X-ray optical system, the level can be adjusted by inserting height-adjusting spacers between the scanning stage 34 and the crystal support table 40.

Next, the scanning motor 38 turns to move the scanning stage 34 in the direction X to position the observing area of the ingot (for example the area near to the tail in the straight cylindrical body) at the X-ray irradiation site. Inasmuch as the crystal orientation can be roughly seen from the habit lines (extending axially) appearing on the periphery of the silicon ingot 22, the φ-rotation motor 44 turns to rotate the silicon ingot on its axis so that the plane (115) of the silicon ingot 22 erects approximately vertically by the help of the habit lines (an azimuth adjustment by φ-rotation).

Figure 8:
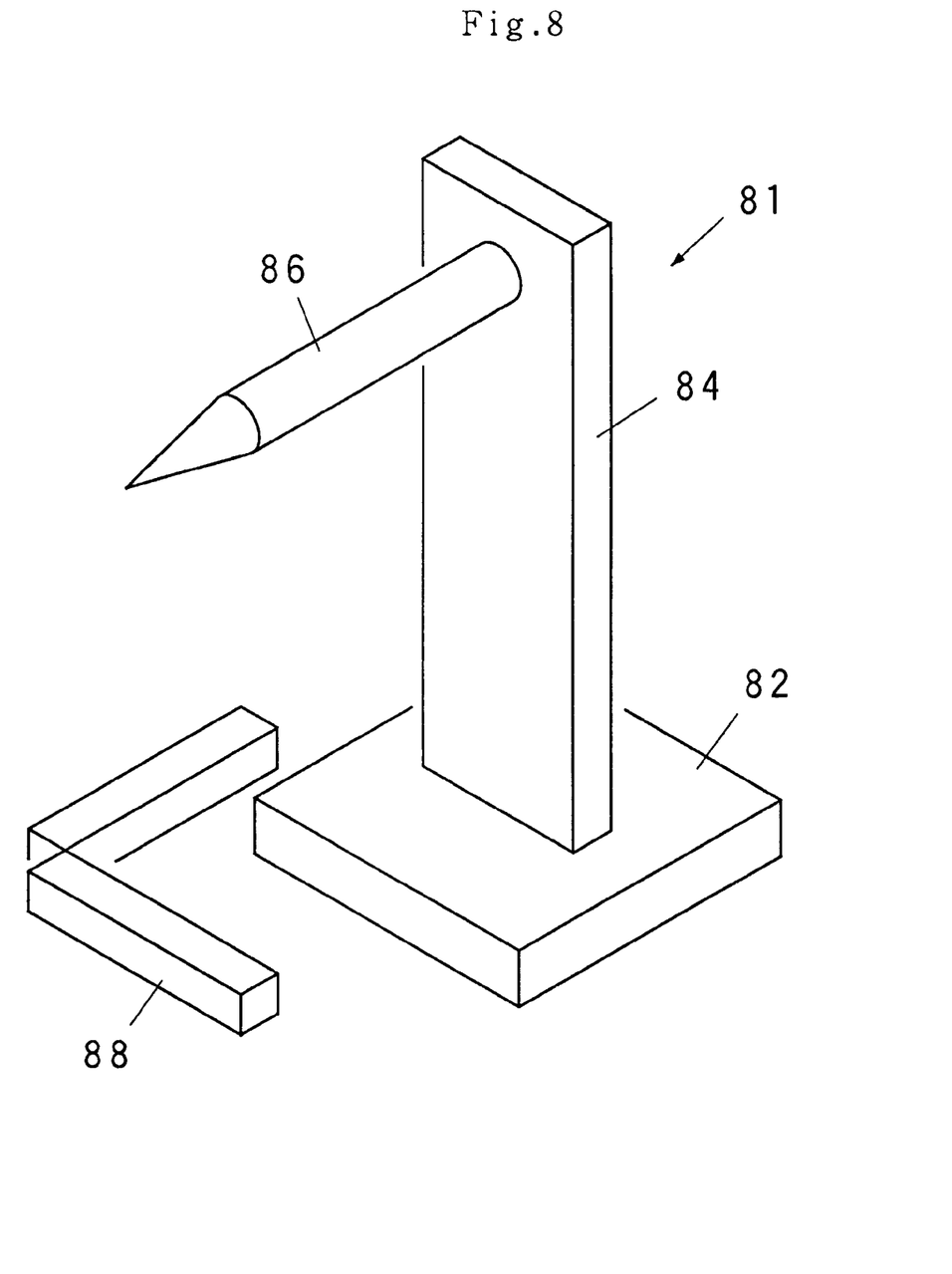
FIG. 8 is a perspective view of a positioning jig for positioning a traveling table.
Figure 9:
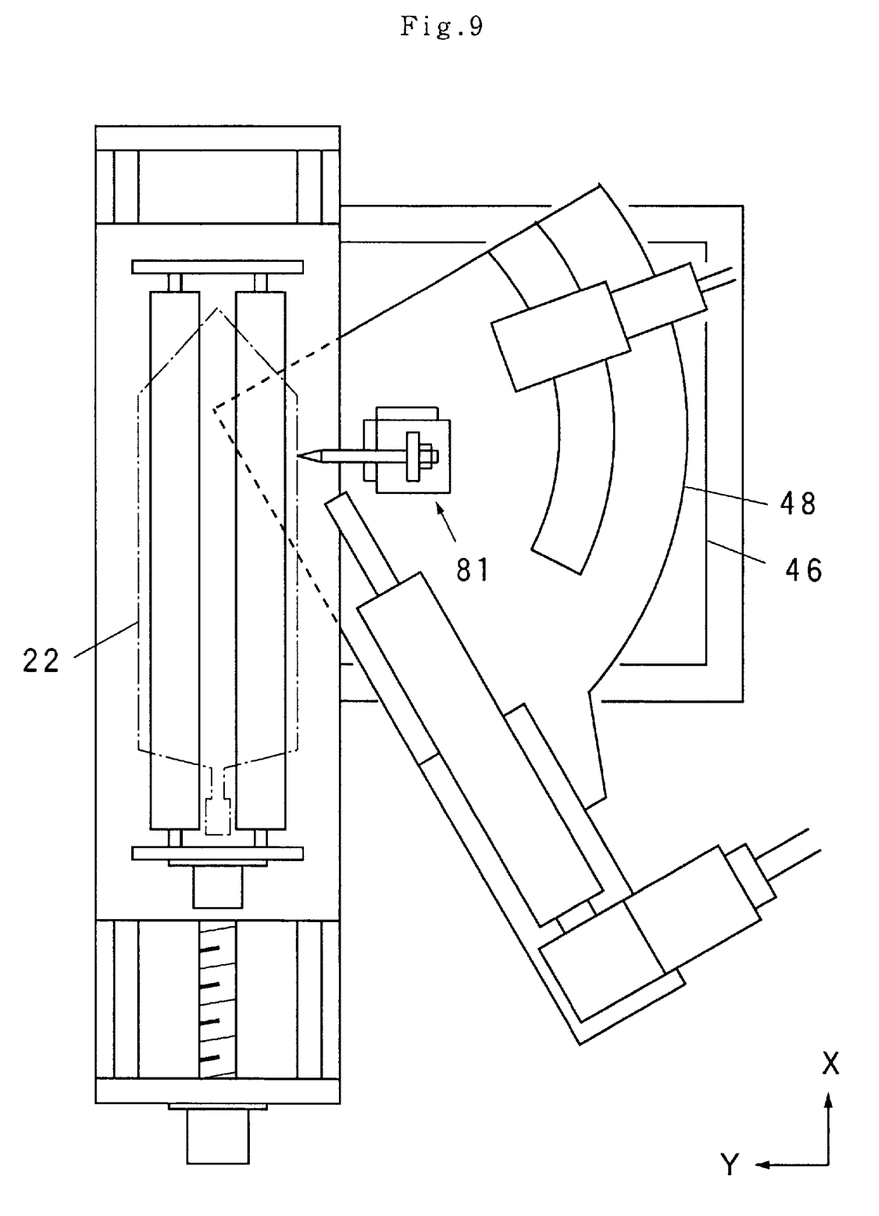
FIG. 9 is a plan view showing the positioning operation of the traveling table.
Figure 10:
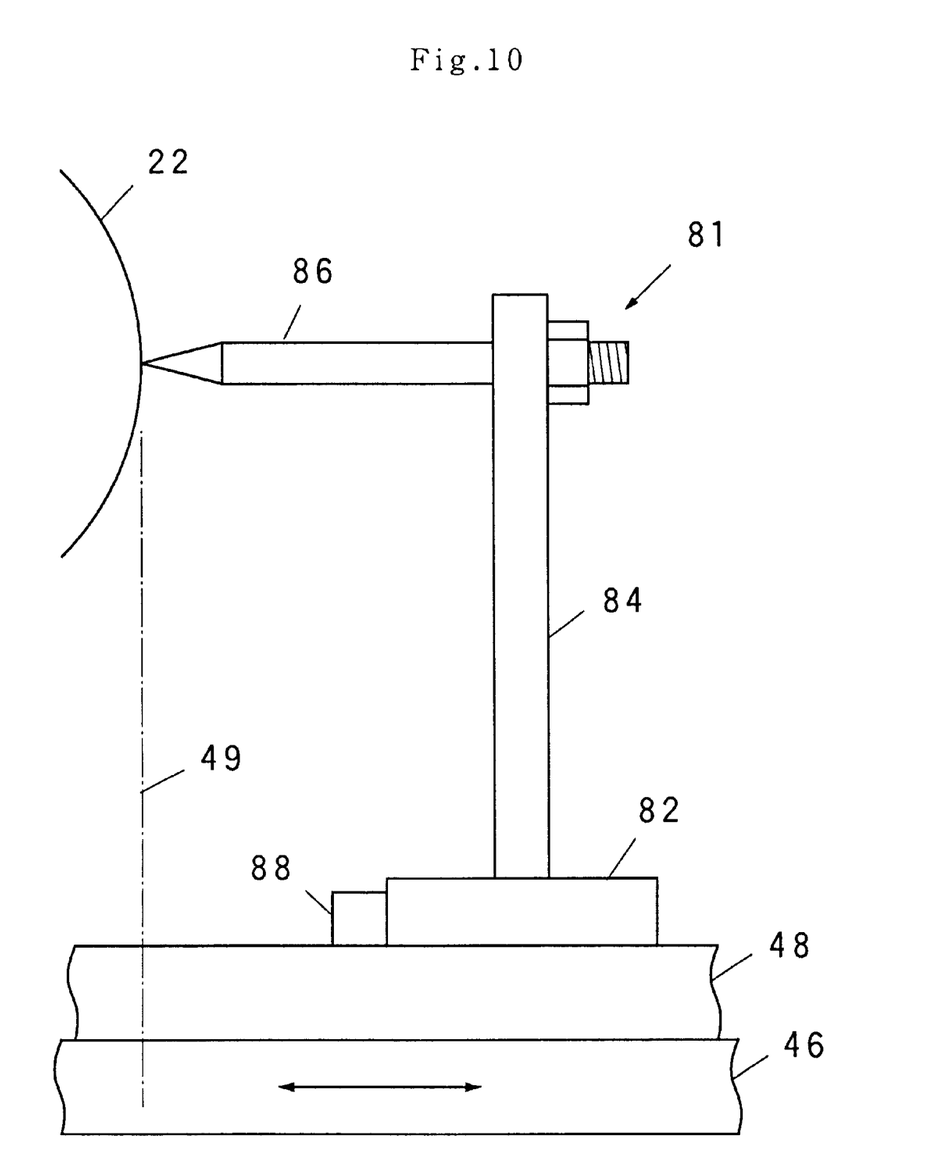
FIG. 10 is an enlarged front view of the positioning operation of the traveling table.

In the next step, the rotation center 49 of the ω-rotation table 48 is positioned at the peripheral surface of the silicon ingot 22 by moving the traveling table 46 in the direction Y. The traveling table 46 is locked by a clamp 47 after the positioning. This positioning work will now be described in more detail hereinafter. FIG. 8 is a perspective view of a jig 81 for positioning the traveling table 46. The positioning jig 81 has a base 82, a support 84 fixed to the base 82, and a pointer 86 horizontally attached near to the top end of the support 84. The base 82 is used for being in contact against an L-shaped reference guide 88 fixed on the top face of the ω-rotation table 48. FIG. 9 is a plan view showing the positioning jig 81 which is set on the ω-rotation table 48, and FIG. 10 is its enlarged front view. As shown in FIG. 10, when the base 82 of the positioning jig 81 is in contact against the reference guide 88 fixed on the top face of the ω-rotation table 48, the tip of the pointer 86 is so positioned as to come just on the rotation center 49 of the ω-rotation table 48, i.e. the pointer length protruding from the support 84 is previously so adjusted. The traveling table 46 is allowed to travel in the direction Y (right to left direction in the figure) so that the tip of the pointer 86 of the positioning jig 81 becomes just in contact with the peripheral surface of the silicon ingot 22, thereby making an alignment between the peripheral surface of the silicon ingot 22 and the rotation center 49 of the ω-rotation table 48.

With the above adjustment, the plane (115) of the silicon ingot and the X-ray optical system become in the positional relationship which satisfies approximately the predetermined diffraction condition. Next, more precise setting for ω-rotation and φ-rotation is carried out while observing the actual diffracted X-rays. The setting will now be described below. In the condition where no fine adjustment has been completed for ω-rotation and φ-rotation, diffracted X-rays (extending vertically in line and being slightly curved) may appear in the monitor display of the X-ray television camera but make no perfect image, i.e. the top and the bottom of of the X-ray irradiation field may be partly cut off or be in no focus. Therefore, ω-rotation and φ-rotation should be alternately adjusted by every a fine angle so as to obtain a clear image from the overall X-ray irradiation field.

In the setting, the ω-rotation table 48 is adjustable by every a fine angle within a range of about 5 degrees by means of a stepping motor. The accuracy of the angle adjustment is 1/1000 degree per one step of the stepping motor. The angle adjustment for φ-rotation is possible by using another stepping motor as well.

Figure 5:
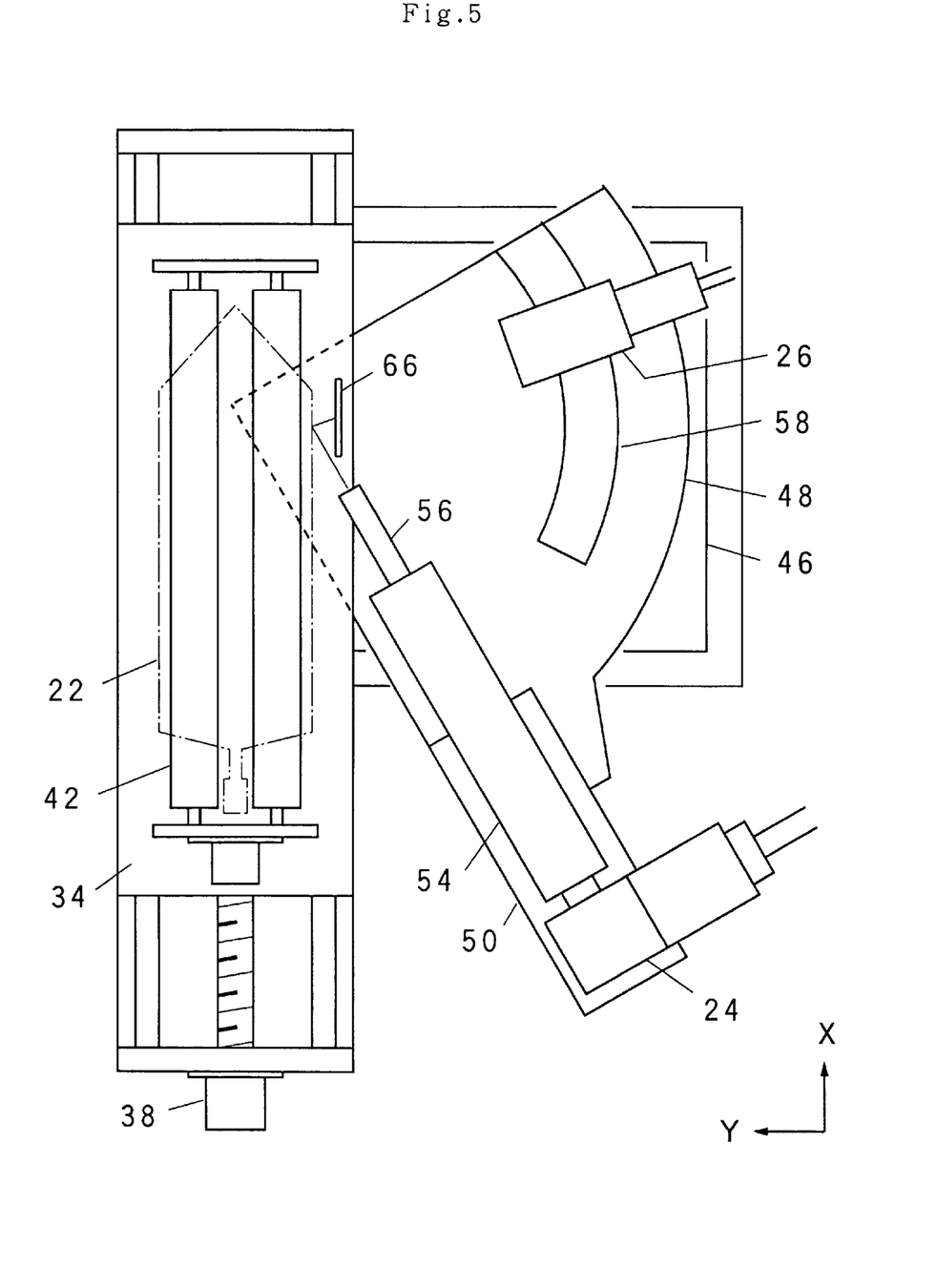
FIG. 5 is a plan view of the apparatus on which the X-ray recording medium is disposed.
Figure 6:
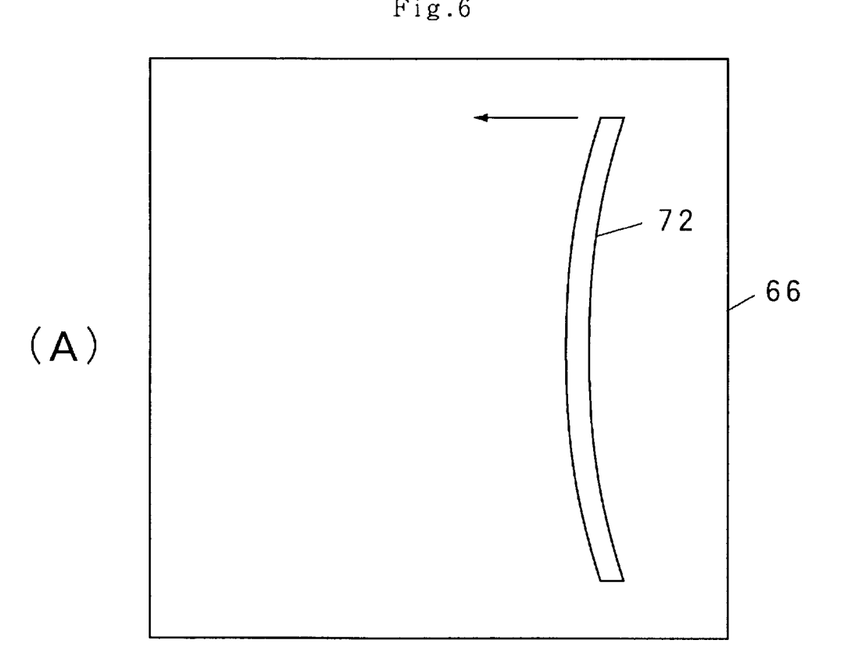

After completion of the setting of the X-ray optical system, the supporting device for the X-ray recording medium shown in FIG. 4 is chucked by the magnet on the scanning stage 34 as shown in FIG. 5 (only the X-ray recording medium 66 is shown in the figure). The distance between the X-ray recording medium 66 and the peripheral surface of the silicon ingot 22 is about 50 mm. The preparations for measurement are thus completed. Then, X-ray topographic images are observed by the steps described below. X-rays from the X-ray source 24 pass through a long evacuated collimator 54 and incident slit 56, and are incident on the peripheral surface of the silicon ingot 22. Diffracted X-rays from the peripheral surface strike the X-ray recording medium 66, so that a slightly-curved and vertically-extending diffraction image 72 is recorded on the X-ray recording medium as shown in FIG. 6(A) (because the incident slit is slightly curved). Then, the scanning stage 34 is scanned (traveling in the direction X) by a predetermined scanning width (tens to 100 mm) while measuring the diffracted X-rays. There is now recorded as shown in FIG. 6(B) a diffraction image 74 corresponding to the scanning width, or an X-ray topographic image of the silicon ingot corresponding to the scanning with. The topographic image recorded on an X-ray film can be visualized by developing the film. In the case where the image is recorded on an imaging plate, the image is excited by a laser beam to generate the fluorescent light with intensity distribution which can be displayed on a display device or printed on a sheet of paper to visualize it.

There are shown in FIG. 6(B) a lot of lines 76 with strong diffraction intensities are observed in the topographic image 74. The lines 76 correspond to the images of the diffracted X-rays from dislocations in the silicon ingot crystal (dislocation images). The dislocation images usually appear in parallel with a given inclined angle. If the observation area of the silicon ingot is properly selected, the dislocation images appear at either right or left side of the topographic image 74 as shown in FIG. 6(B), showing no dislocation images at the other side as shown. This means that a proper choice of the observation area makes it possible to detect the boundary 78 between a dislocation-appearing area and a dislocation-disappearing area. If the entire topographic image 74 is covered with only any one of a dislocation-appearing area and a dislocation-disappearing area, the silicon ingot should be shifted along its axis to obtain other topographic images again until the boundary 78 is detected.

When the silicon ingot is cut off at the boundary 78 (or at a position slightly shifted to a dislocation-disappearing side from the boundary), a useful crystal of good quality can be obtained with no loss. When a marker 80 is painted on the peripheral surface of the silicon ingot, the marker 80 is also recorded on the X-ray topographic image. Therefore, the determination of the position of the boundary 78 on the periphery of the silicon ingot is based on this marker 80.

After the boundary between a dislocation-appearing area and a dislocation-disappearing area have been found by observing the X-ray topographic image near to the tail in the straight cylindrical body of the silicon ingot, the scanning stage is moved to find the other boundary as well near to the shoulder in the straight cylindrical body, thereby precisely determining two cutting positions of the silicon ingot.

What is claimed is:

1. An X-ray topographic method for minding a boundary between a dislocation-appearing area and a dislocation-disappearing area in an unprocessed single crystal ingot as it is after being produced by Czochralski method, comprising the steps of:

(a) supporting the unprocessed single crystal ingot rotatably on its axis and movably along its axis;

(b) irradiating X-rays to a peripheral surface of the ingot through an incident slit having a long and narrow opening, and obtaining an image of diffracted X-rays from the ingot with an X-ray television camera, followed by setting positional relationship between the ingot and an X-ray optical system so that an optimum image could be obtained;

(c) disposing a two-dimensional X-ray recording medium at a position where the diffracted X-rays can be detected;

(d) irradiating X-rays to the peripheral surface of the ingot through the incident slit, and scanning the ingot synchronously with the X-ray recording medium in an axial direction of the ingot while recording diffracted X-rays from the ingot; and (e) finding a boundary between a dislocation-appearing area and a dislocation-disappearing area by observing a topographic image recorded on the X-ray recording medium.

2. An X-ray topographic method according to claim 1, wherein any two-dimensional X-ray imaging device for setting is used instead of the X-ray television camera.

3. An X-ray topographic method according to claim 2, wherein any two-dimensional X-ray imaging device for observing X-ray topographic images is used instead of the X-ray recording medium.

4. An X-ray topographic method according to claim 3, wherein the two-dimensional X-ray imaging device for setting is used also as the two-dimensional X-ray imaging device for observing X-ray topographic images.

5. An X-ray topographic method according to claim 3 wherein the two-dimensional X-ray imaging device for observing X-ray topographic images is a camera device capable of obtaining X-ray images as electronic signals, and output signals of the camera device is stored into different memory areas in every given sampling time during scanning the ingot, instead of scanning the X-ray recording medium synchronously with the ingot.

6. An X-ray topographic apparatus for finding a boundary between a dislocation-appearing area and a dislocation-disappearing area in an unprocessed single crystal ingot as it is after being produced by Czochralski method, comprising:

(a) two parallel rollers for supporting thereon the unprocessed single crystal ingot rotatably around an axis of the ingot;

(b) a scanning stage having the rollers;

(c) a scanning mechanism for traveling the scanning stage in an axial direction of the ingot;

(d) an incident X-ray optical system including an X-ray source, a collimator connected to the X-ray source, and an incident slit fixed to a tip of the collimator, wherein the incident slit has a long and narrow opening perpendicular to a traveling direction of the scanning stage;

(e) an X-ray television camera for obtaining an image of diffracted X-rays from the ingot for the use of setting of an X-ray optical system;

(f) a two-dimensional X-ray recording medium for recording the diffracted X-rays from the ingot for the use of recording of an X-ray topographic image;

(g) a medium cassette which can support the X-ray recording medium, wherein the X-ray recording medium is positioned selectively in a position on a light path of diffracted X-rays and in a position out of the light path of the diffracted X-rays;

(h) a rotary table on which the incident X-ray optical system and the X-ray television camera are mounted, the rotary table being rotatable around a rotation center;

(i) an angle-adjustment device allowing the X-ray television camera to rotate on the rotary table around the rotation center so as to adjust an rotary angle; and (j) a traveling table on which the rotary table is mounted, the traveling table being movable in a direction perpendicular to the traveling direction of the scanning stage.

7. An X-ray topographic method according to claim 4 wherein the two-dimensional X-ray imaging device for observing X-ray topographic images is a camera device capable of obtaining X-ray images as electronic signals, and output signals of the camera device is stored into different memory areas in every given sampling time during scanning the ingot, instead of scanning the X-ray recording medium synchronously with the ingot.

* * * * *

UNITED STATES PATENT AND TRADEMARK OFFICE
CERTIFICATE OF CORRECTION

PATENT NO. : 6,072,854  
DATED : June 6, 2000  
INVENTOR(S) : Kikuchi et al.

Page 1 of 1

It is certified that error appears in the above-identified patent and that said Letters Patent is hereby corrected as shown below:

Column 7,  
Line 67, (claim 1, line 1), change "minding" to -- finding --;

Column 9,  
Line 11, change "an" to -- a --.

Signed and Sealed this

Thirteenth Day of November, 2001

Attest:

*Nicholas P. Godici*

NICHOLAS P. GODICI  
*Acting Director of the United States Patent and Trademark Office*

*Attesting Officer*